US011215531B2

(12) United States Patent
Morishita (10) Patent No.: US 11,215,531 B2
(45) Date of Patent: Jan. 4, 2022

(54) OXYGEN SENSOR CONTROL DEVICE WITH DETECTION SWITCHING BASED ON IMPEDANCE STATE

(71) Applicant: DENSO CORPORATION, Kariya (JP)

(72) Inventor: Koji Morishita, Kariya (JP)

(73) Assignee: DENSO CORPORATION, Kariya (JP)

(*) Notice: Subject to any disclaimer, the term of this patent is extended or adjusted under 35 U.S.C. 154(b) by 301 days.

(21) Appl. No.: 16/448,370

(22) Filed: Jun. 21, 2019

(65) Prior Publication Data
US 2020/0049590 A1 Feb. 13, 2020

(30) Foreign Application Priority Data
Aug. 10, 2018 (JP) .............................. JP2018-151309

(51) Int. Cl.
*G01M 15/10* (2006.01)
*G01N 33/00* (2006.01)
*G01N 27/02* (2006.01)

(52) U.S. Cl.
CPC ........ *G01M 15/104* (2013.01); *G01N 27/028* (2013.01); *G01N 33/0073* (2013.01)

(58) Field of Classification Search
CPC ............ G01M 15/104; G01N 33/0073; G01N 27/028
See application file for complete search history.

(56) References Cited

U.S. PATENT DOCUMENTS

| 2015/0219590 A1 | 8/2015 | Uemura et al. |
| 2015/0293044 A1 | 10/2015 | Uemura |
| 2015/0323493 A1* | 11/2015 | Uemura .................. F02D 41/28 204/406 |
| 2015/0362457 A1 | 12/2015 | Watanabe |
| 2016/0123922 A1 | 5/2016 | Akimoto et al. |

* cited by examiner

*Primary Examiner* — Eric S. McCall
*Assistant Examiner* — Timothy P Graves
(74) *Attorney, Agent, or Firm* — Posz Law Group, PLC (57) ABSTRACT

A voltage application detection unit detects an impedance of an oxygen sensor, which outputs a signal corresponding to a concentration of oxygen, based on a current change amount in the oxygen sensor caused by application of a voltage to the oxygen sensor. A current application detection unit detects the impedance based on a voltage change amount generated across the oxygen sensor caused by application of a current to the oxygen sensor. A detection switching unit switches between the voltage application detection unit and the current application detection unit to detect the impedance based on a state of the oxygen sensor.

9 Claims, 7 Drawing Sheets

OXYGEN SENSOR CONTROL DEVICE WITH DETECTION SWITCHING BASED ON IMPEDANCE STATE

CROSS REFERENCE TO RELATED APPLICATION

The present application claims the benefit of priority from Japanese Patent Application No. 2018-151309 filed on Aug. 10, 2018. The entire disclosure of the above application is incorporated herein by reference.

TECHNICAL FIELD

The present disclosure relates to an oxygen sensor control device configured to control an oxygen sensor.

BACKGROUND

Conventionally, an oxygen sensor has been widely used in, for example, an internal combustion engine to detect a concentration of oxygen in exhaust gas.

SUMMARY

According to an aspect of the present disclosure, an oxygen sensor control device is configured to control an oxygen sensor. The oxygen sensor is configured to output a signal corresponding to a concentration of oxygen. The oxygen sensor control device is configured to detect an impedance of the oxygen sensor.

BRIEF DESCRIPTION OF THE DRAWINGS

The above and other objects, features and advantages of the present invention will become more apparent from the following detailed description made with reference to the accompanying drawings. In the drawings.

DETAILED DESCRIPTION

To begin with, examples of the present disclosure will be described.

According to an example of the present disclosure, an oxygen sensor of a limiting current type has a configuration to allow a limiting current of a constant value to flow therethrough regardless of a magnitude of the voltage on application of a voltage in a predetermined voltage range to the oxygen sensor of the limiting current type. The magnitude of the limiting current varies with a concentration of oxygen.

According to an example of the present disclosure, a control device is employable to control the voltage applied to such an oxygen sensor thereby to detect the concentration of oxygen. In an assumable configuration, the control device may apply a voltage to the oxygen sensor to cause the limiting current to flow in the oxygen sensor and to detect the concentration of oxygen based on the magnitude of the limiting current. In the configuration, the control device estimates a temperature of the oxygen sensor to use the temperature of the oxygen sensor for control according to the voltage applied to the oxygen sensor or for control according to a temperature of a heater for heating the oxygen sensor. In the configuration, the control device estimates the temperature of the oxygen sensor based on an impedance of the oxygen sensor. In addition, the control device calculates the impedance of the oxygen sensor based on a variation width of the current associated with the application of the voltage to the oxygen sensor. A voltage that varies in magnitude with time and is applied at the time of impedance detection is defined as a sweep voltage.

In an assumable configuration, a control device may detect the impedance of the oxygen sensor only by detecting the voltage application, which is calculated on the basis of the variation range of the current associated with the application of the voltage. Therefore, in the assumable configuration, the control device would degrade in detection accuracy of the impedance when the oxygen sensor becomes unsuitable for voltage application detection.

According to one aspect of the present disclosure, an oxygen sensor control device is configured to control an oxygen sensor. The oxygen sensor is configured to output a signal corresponding to a concentration of oxygen. The oxygen sensor control device comprises a voltage application detection unit configured to detect an impedance of the oxygen sensor based on a current change amount in the oxygen sensor caused by application of a voltage to the oxygen sensor. The oxygen sensor control device further comprises a current application detection unit configured to detect the impedance based on a voltage change amount generated across the oxygen sensor caused by application of a current to the oxygen sensor. The oxygen sensor control device further comprises a detection switching unit configured to switch between the voltage application detection unit and the current application detection unit to detect the impedance based on a state of the oxygen sensor.

According to the one aspect, the detection switching unit is configured to switch between the voltage application detection unit and the current application detection unit to detect the impedance. As a result, the control device could be enabled to detect the impedance by using an appropriate one of the voltage application detection unit and the current application detection unit according to the state of the oxygen sensor. Therefore, the control device could be enabled to inhibit a decrease in the detection accuracy of the impedance of the oxygen sensor.

Hereinafter, multiple embodiments of the present disclosure will be described with reference to the drawings. In the description of each embodiment, the corresponding components are denoted by the same reference numerals, and a repetitive description of the corresponding components may be omitted. When only a portion of the configuration is described, the embodiments described above may be applied to other portions of the configuration. Further, not only the combinations of the configurations explicitly shown in the description of the respective embodiments, but also a partial combination of the configurations may be enabled even if the combinations are not explicitly shown unless a problem arises in particular.

First Embodiment

Figure 1:
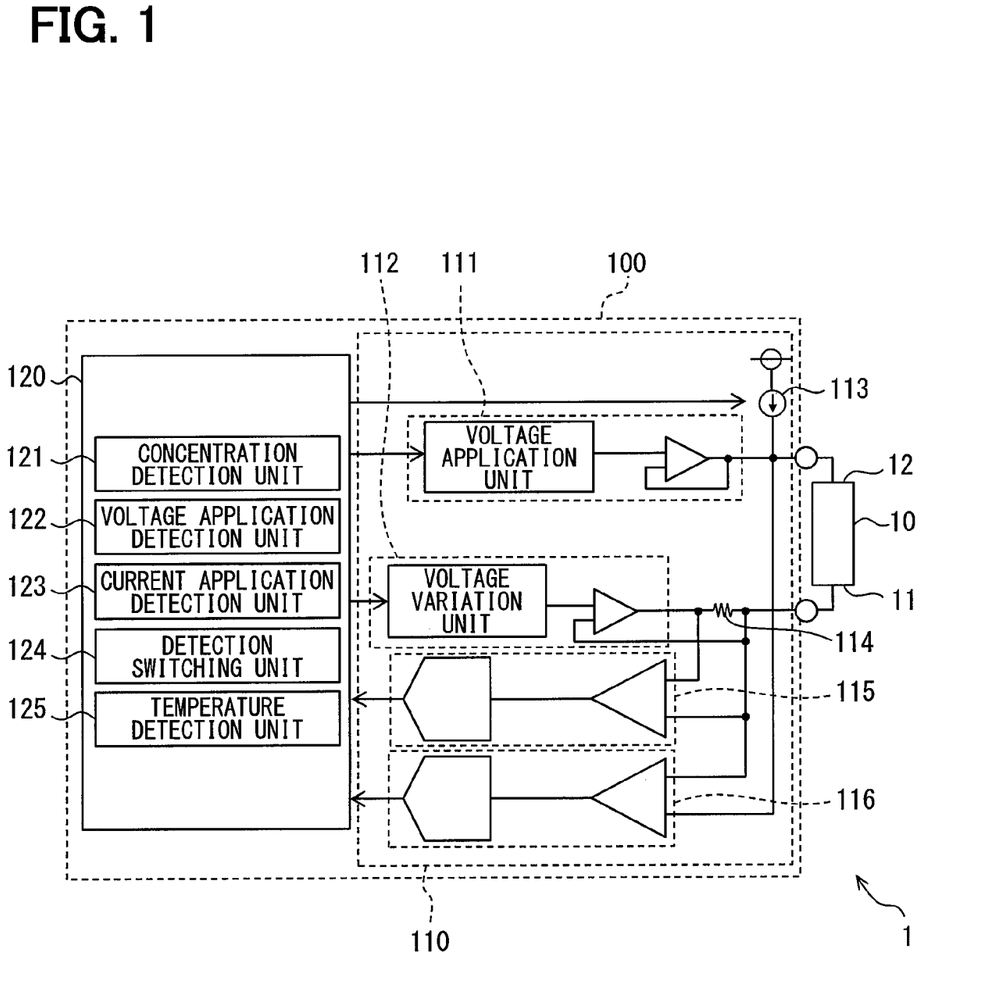
FIG. 1 is a diagram showing a configuration of a control device and a connection relationship with an air-fuel ratio sensor (oxygen sensor).

A control device 100 according to a first embodiment of the present disclosure is used in a sensor system 1 as shown in FIG. 1. The sensor system 1 is used for detecting an air-fuel ratio of an engine in, for example, a hybrid vehicle including an engine and a motor as a travel driving source. Specifically, the sensor system 1 detects the air-fuel ratio based on the concentration of oxygen or unburned gas that has fluctuated according to the air-fuel ratio in the exhaust from the engine. The sensor system 1 includes an air-fuel ratio sensor 10 in addition to the control device 100.

The air-fuel ratio sensor 10 is a so-called limiting current type sensor. When a voltage within a predetermined range is applied to the air-fuel ratio sensor 10, a limiting current of a substantially constant magnitude flows in the air-fuel ratio sensor 10 regardless of the magnitude of the voltage. The air-fuel ratio sensor 10 corresponds to an "oxygen sensor" that outputs the limiting current as a signal corresponding to the concentration of oxygen. The air-fuel ratio sensor 10 is formed by stacking a solid electrolyte layer made of zirconia or the like, a diffusion resistance layer made of porous ceramic or the like, an electrode sandwiching the solid electrolyte layer, a heater, and the like. An exhaust gas is supplied to an exhaust side electrode 11 which is one of the electrodes. The supply amount of the exhaust gas is limited by the diffusion resistance layer. Atmosphere is supplied to an atmosphere side electrode 12 which is the other of the electrodes.

The solid electrolyte layer allows ionized oxygen to pass through the solid electrolyte layer in a state of being heated by an exhaust gas or a heater. A current flows through the solid electrolyte layer in accordance with the amount of oxygen, which has passed through the solid electrolyte layer. When the air-fuel ratio is leaner than a theoretical air-fuel ratio, the amount of oxygen that passes from the exhaust-side electrode 11 through the solid electrolyte layer and moves to the atmosphere side electrode 12 depends on the amount of oxygen supplied to the exhaust side electrode 11, that is, the concentration of oxygen remaining in the exhaust gas. When the air-fuel ratio is richer than the theoretical air-fuel ratio, the amount of oxygen that moves from the atmosphere side electrode 12 to the exhaust-side electrode 11 depends on the amount of unburned gas that is able to react with the oxygen that has moved to the exhaust side electrode 11, that is, the concentration of the unburned gas in the exhaust gas. As a result, the air-fuel ratio sensor 10 outputs a limiting current having a magnitude according to the oxygen concentration and the unburned gas concentration in the exhaust gas. Therefore, the air-fuel ratio sensor 10 outputs a limiting current corresponding to the air-fuel ratio.

Figure 2:
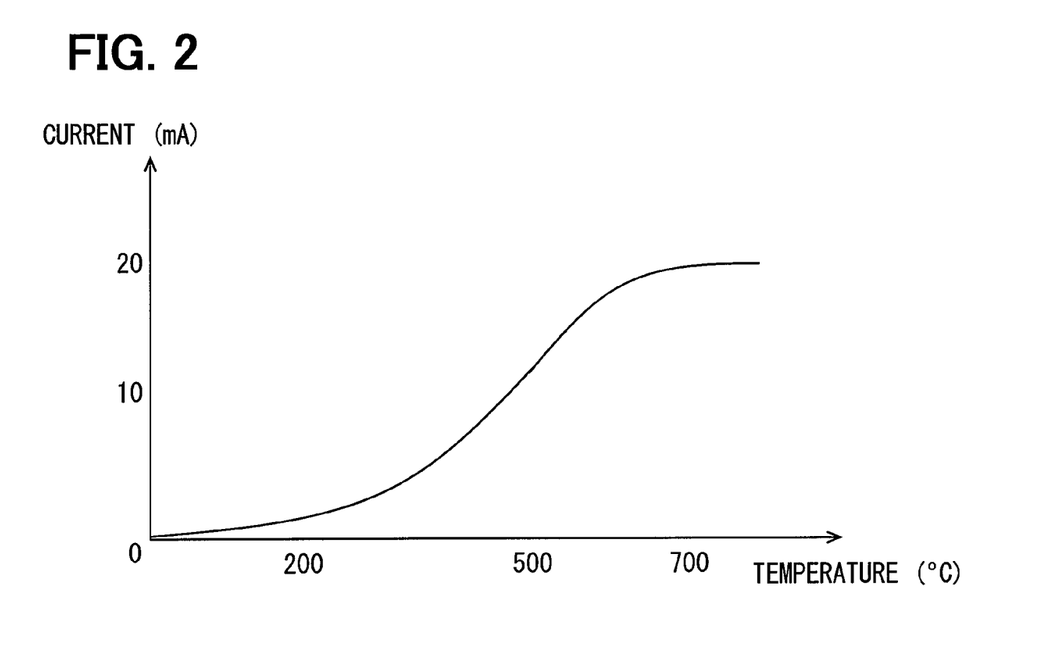
FIG. 2 is a diagram showing a relationship between a temperature of an air-fuel ratio sensor and a maximum value of a flowing current.
Figure 3:
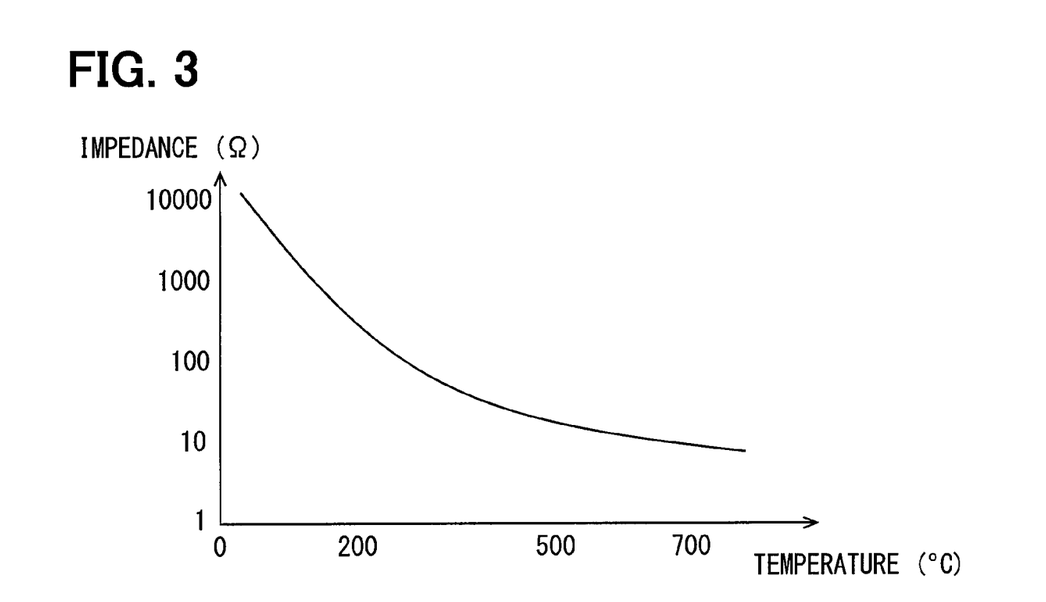
FIG. 3 is a diagram showing a relationship between the temperature and an impedance of the air-fuel ratio sensor.

The air-fuel ratio sensor 10 may be at a low temperature in a state in which heating by the exhaust gas or a heater is stopped. As the temperature of the air-fuel ratio sensor 10 decreases more, a transfer rate of oxygen passing through the solid electrolyte layer decreases more. As the transfer rate of oxygen decreases, as shown in FIG. 2, a maximum value of the current flowing by application of a predetermined voltage decreases. For example, at a temperature of 500 to 600° C. or higher, a so-called active state in which a current is able to flow up to the limiting current is obtained. Below the temperature at which the active state occurs, a so-called inactive state occurs in which the current does not flow up to the limiting current due to the decrease of the current. Further, as the transfer rate of oxygen decreases more, an impedance of the air-fuel ratio sensor 10 increases more as shown in FIG. 3. The impedance of the air-fuel ratio sensor 10 increases exponentially as the temperature decreases.

The control device 100 is, for example, as shown in FIG. 1, an electronic control device realized as a microcontroller in which an input and output unit 110, a calculation unit 120, a memory, and the like are integrated on a semiconductor substrate. The control device 100 corresponds to an "oxygen sensor control device". The control device 100 controls the air-fuel ratio sensor 10 to perform a function of detecting the air-fuel ratio with the execution of software stored in the memory by the calculation unit 120. The control device 100 may be realized by hardware including a part or all of the functions performed by the calculation unit 120. The input and output unit 110 includes a voltage application unit 111, a voltage variation unit 112, a current application unit 113, a shunt resistor 114, a current detection unit 115, and a voltage detection unit 116. The functions exhibited by the calculation unit 120 include functions as a concentration detection unit 121, a voltage application detection unit 122, a current application detection unit 123, a detection switching unit 124, and a temperature detection unit 125.

The voltage application unit 111 includes a buffer circuit such as an operational amplifier. The voltage application unit 111 is connected to the atmosphere side electrode 12. The voltage application unit 111 provides a predetermined potential to the atmosphere side electrode 12.

Figure 4:
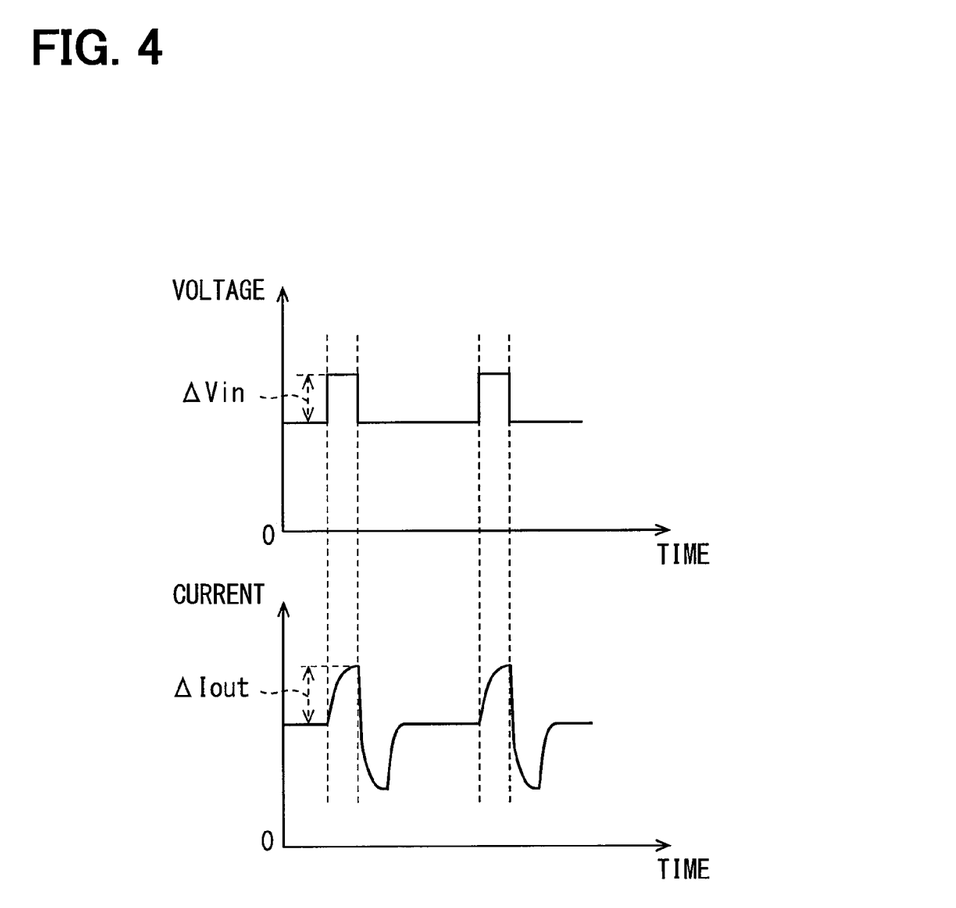
FIG. 4 is a diagram showing variations in voltage and current due to application of a voltage.

The voltage variation unit 112 includes a buffer circuit including an operational amplifier and the like. The voltage variation unit 112 is connected to the exhaust side electrode 11 through a shunt resistor 114, which will be described later. The voltage variation unit 112 provides a potential lower than that of the voltage application unit 111 to the exhaust side electrode 11. The voltage variation unit 112 temporally varies a potential at the exhaust side electrode 11. As a result, the voltage variation unit 112 applies a sweep voltage, which is a voltage varying over time, to the air-fuel ratio sensor 10. Specifically, the voltage variation unit 112 sets the potential provided to the exhaust side electrode 11 as a pulse varying in a rectangular wave shape, for example. As a result, the voltage applied to the air-fuel ratio sensor 10 becomes a sweep voltage which fluctuates in a pulse shape with the passage of time as shown in FIG. 4. As the sweep voltage is applied, the current flowing through the air-fuel ratio sensor 10 also fluctuates with time. A current change amount $\Delta$Iout associated with the application of the sweep voltage is a magnitude obtained by dividing the voltage change amount $\Delta$Vin of the sweep voltage by the impedance of the air-fuel ratio sensor 10.

Figure 5:
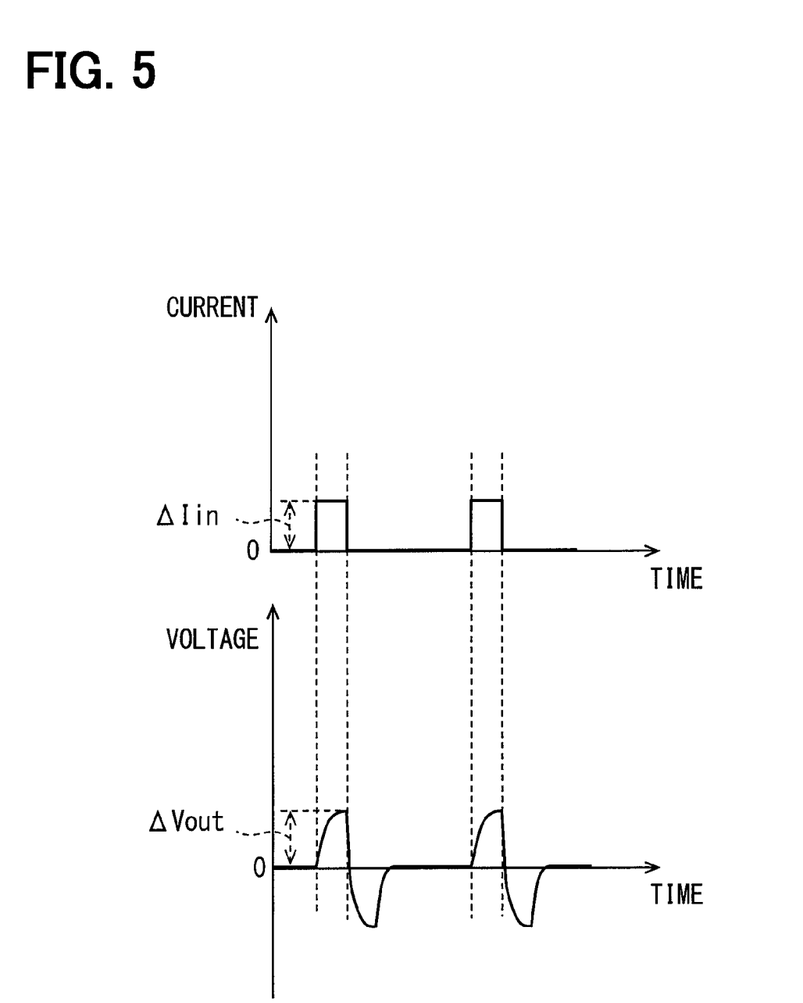
FIG. 5 is a diagram showing variations in current and voltage due to application of a current.

The current application unit 113 includes a current output circuit. The current application unit 113 is connected to the atmosphere side electrode 12. The current application unit 113 applies a current to the air-fuel ratio sensor 10. Specifically, the current application unit 113 applies a substantially constant current at a predetermined magnitude. When the constant current by the current application unit 113 is applied to the air-fuel ratio sensor 10 in which no current flows, the current flowing in the air-fuel ratio sensor 10 fluctuates in a pulse shape exhibiting a rectangular wave shape as shown in FIG. 5. Along with such a variation in the current, the voltage generated across the air-fuel ratio sensor 10 also varies with time. The voltage change amount ΔVout associated with the current application is a current change amount ΔIin, that is, a magnitude obtained by multiplying the magnitude of the supplied constant current by the impedance of the air-fuel ratio sensor 10.

The shunt resistor 114 is connected to the exhaust side electrode 11 in series with the air-fuel ratio sensor 10. A current having substantially the same magnitude as the current flowing through the air-fuel ratio sensor 10 flows through the shunt resistor 114. A voltage proportional to the current flowing through the air-fuel ratio sensor 10 is generated across the shunt resistor 114.

The current detection unit 115 includes an AD converter for performing an analog-to-digital conversion, and so on. The current detection unit 115 detects a voltage generated across the shunt resistor 114, thereby detecting a current flowing through the air-fuel ratio sensor 10, and inputs the current to the calculation unit 120.

The voltage detection unit 116 includes an AD converter and the like. The voltage detection unit 116 detects a voltage generated at both ends of the air-fuel ratio sensor 10, that is, between the exhaust side electrode 11 and the atmosphere side electrode 12, and inputs the voltage to the calculation unit 120.

The concentration detection unit 121 detects an air-fuel ratio corresponding to the concentration of oxygen based on the concentration detection current flowing through the air-fuel ratio sensor 10 in response to the application of a predetermined voltage. Specifically, the concentration detection unit 121 applies a predetermined voltage to the air-fuel ratio sensor 10 as a difference in potential between the voltage application unit 111 and the voltage variation unit 112. A limiting current flows through the air-fuel ratio sensor 10 by application of the predetermined voltage. The concentration detection unit 121 determines that the concentration detection current detected by the current detection unit 115 corresponds to the limiting current, and detects the air-fuel ratio in accordance with a correspondence relationship between the limiting current stored in the memory and the air-fuel ratio.

The voltage application detection unit 122 detects the impedance of the air-fuel ratio sensor 10 based on the current change amount in the air-fuel ratio sensor 10 caused by the application of the voltage. The voltage application detection unit 122 controls the voltage application unit 111 and the voltage variation unit 112 to apply the sweep voltage to the air-fuel ratio sensor 10. The voltage application detection unit 122 acquires the current change amount ΔIout based on the variation of the current detected by the current detection unit 115. The voltage application detection unit 122 detects a value obtained by dividing the voltage change amount ΔVin of the sweep voltage by the current change amount ΔIout as the impedance of the air-fuel ratio sensor 10.

The current application detection unit 123 detects the impedance of the air-fuel ratio sensor 10 based on the voltage generated at both ends of the air-fuel ratio sensor 10 according to the application of the current. The current application detection unit 123 controls the current application unit 113 to apply a constant current to the air-fuel ratio sensor 10. The current application detection unit 123 acquires the voltage change amount ΔVout based on the variation of the voltage detected by the voltage detection unit 116. The current application detection unit 123 detects, as the impedance of the air-fuel ratio sensor 10, a value obtained by dividing the acquired voltage change amount ΔVout by the current change amount ΔIin, that is, the magnitude of the constant current.

Figure 6:
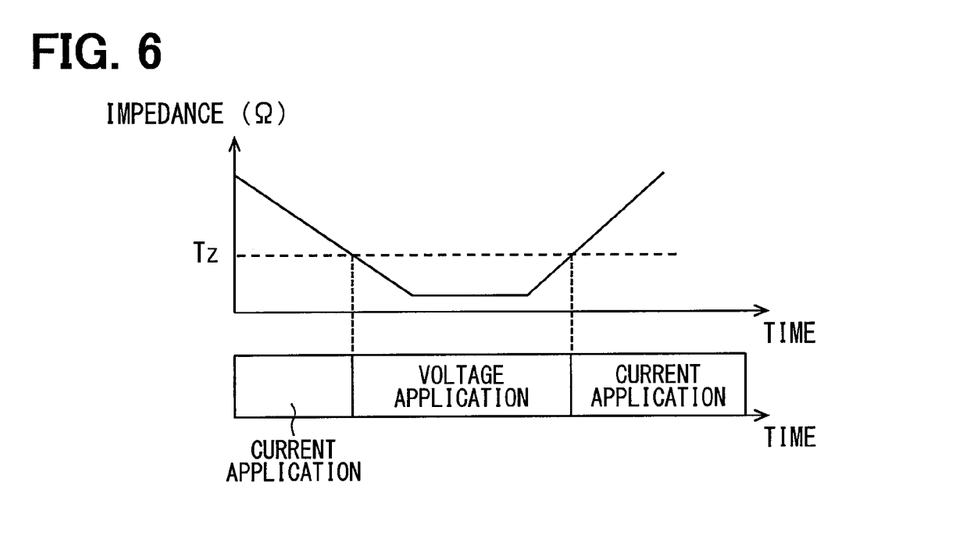
FIG. 6 is a diagram showing an example of the switching behavior in the first embodiment.

The detection switching unit 124 switches between the voltage application detection unit 122 and the current application detection unit 123 based on the state of the air-fuel ratio sensor 10 to detect the impedance. The detection switching unit 124 switches a detection unit that next detects the impedance in the voltage application detection unit 122 and the current application detection unit 123 based on the detected impedance. The detection switching unit 124 performs switching based on whether the detected impedance is in a high impedance state equal to or higher than an impedance threshold Tz or a low impedance state lower than the impedance threshold, as shown in FIG. 6.

The impedance threshold Tz is set to, for example, an impedance at a minimum temperature at which the air-fuel ratio sensor 10 can be regarded as an active state, and is stored in the memory. The detection switching unit 124 detects the impedance in the current application detection unit 123 when the detected impedance is in the high impedance state. The detection switching unit 124 causes the voltage application detection unit 122 to detect the impedance when the impedance is in the low impedance state.

The temperature detection unit 125 detects the temperature of the air-fuel ratio sensor 10 based on the impedance detected by the detection switching unit 124. The temperature detection unit 125 detects the temperature of the air-fuel ratio sensor 10 based on the correspondence relationship between the impedance and the temperature stored in the memory. The temperature detected by the temperature detection unit 125 is used for, for example, operation control of a heater that heats the air-fuel ratio sensor 10 to an active state. The operation of the heater is controlled so that the detected temperature becomes the target temperature. The target temperature is preset to a temperature at which the air-fuel ratio sensor 10 is in an active state and stored in the memory.

An example of a processing procedure in the calculation unit 120 will be described. For example, when the engine is operating, the calculation unit 120 periodically executes the processing shown in FIG. 7 in order from S1.

Figure 7:
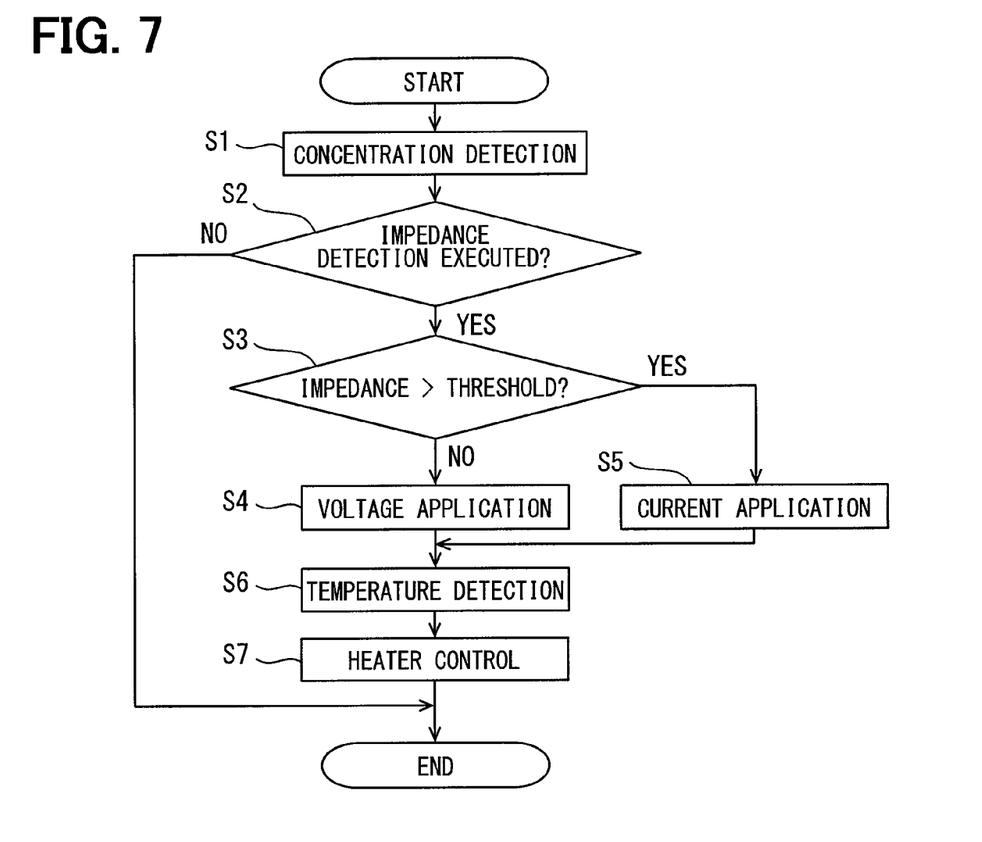
FIG. 7 is a flowchart showing the processing of a calculation unit according to a first embodiment.

In S1, the oxygen concentration of the exhaust gas is detected by processing corresponding to the concentration detection unit 121. In S2, it is determined whether or not a condition for executing the impedance detection is satisfied. The condition for executing the impedance detection is, for example, a case in which a predetermined time has elapsed from the latest detection. When the condition is satisfied, the routine proceeds to S3, and when the condition is not satisfied, the process shown in FIG. 7 is terminated.

In S3, it is determined whether or not the impedance detected most recently is equal to or greater than an impedance threshold by the processing corresponding to the detection switching unit 124. If the impedance is not equal to or greater than the impedance threshold, the routine proceeds to S4, and if the impedance is equal to or greater than the impedance threshold, the routine proceeds to S5. If the state is immediately after the start of the periodic execution of FIG. 7, it is determined that the impedance value is equal to or greater than the impedance threshold, and the routine proceeds to S5.

In S4, the impedance is detected by a process corresponding to the voltage application detection unit 122, and the routine proceeds to S6. In S5, the impedance is detected by a process corresponding to the current application detection unit 123, and the routine proceeds to S6.

In S6, the temperature is detected by a process corresponding to the temperature detection unit 125. More specifically, the temperature is detected based on the impedance detected in S4 or S5 in the latest. In S7, the operation control of the heater is performed based on the temperature detected in the most recent S6.

According to the first embodiment described above, the detection switching unit 124 switches between the voltage application detection unit 122 and the current application detection unit 123 to detect the impedance. As a result, the control device 100 is configured to detect the impedance by an appropriate one of the voltage application detection unit 122 and the current application detection unit 123 according to the state of the air-fuel ratio sensor 10. Therefore, the control device 100 is configured to inhibit a decrease in the detection accuracy of the impedance of the air-fuel ratio sensor 10.

The detection switching unit 124 according to the present embodiment switches between the voltage application detection unit 122 and the current application detection unit 123 based on the impedance. As a result, the control device 100 is configured to detect the impedance of the air-fuel ratio sensor 10 by an appropriate one of the voltage application detection unit 122 and the current application detection unit 123 in accordance with the impedance of the air-fuel ratio sensor 10. Therefore, the control device 100 is configured to inhibit a decrease in the detection accuracy of the impedance of the air-fuel ratio sensor 10.

The detection switching unit 124 switches between the current application detection unit 123 and the voltage application detection unit 122 based on whether the detected impedance is in the high impedance state or the low impedance state. As a result, the control device 100 is configured to detect the impedance of each of the high impedance state and the low impedance state by an appropriate one of the voltage application detection unit 122 and the current application detection unit 123. Therefore, the control device 100 is configured to inhibit a decrease in the detection accuracy of the impedance of the air-fuel ratio sensor 10.

Further, according to the switching described above, the current application detection unit 123 and the voltage application detection unit 122 detect the impedance in either the high impedance state or the low impedance state, respectively. This makes it possible to reduce a difference between a lower limit of the impedance that needs to be detected with the use of the current application detection unit 123 and an upper limit of the impedance that needs to be detected with the use of the voltage application detection unit 122. Therefore, the voltage change amount $\Delta$Vout and the current change amount $\Delta$Iout used for the detection can reduce an error in the detection. Therefore, the control device 100 is configured to inhibit a decrease in the detection accuracy of the impedance of the air-fuel ratio sensor 10.

The detection switching unit 124 switches to the current application detection unit 123 in the high impedance state and switches to the voltage application detection unit 122 in the low impedance state. In this example, the voltage generated in the air-fuel ratio sensor 10 by the application of the current of a predetermined value is larger in the high impedance state than in the low impedance state. Therefore, the current application detection unit 123 switched in the high impedance state can accurately detect the generated voltage and accurately detect the impedance. The amount of change in the current flowing through the air-fuel ratio sensor 10 by the application of the sweep voltage is larger in the low impedance state than in the high impedance state. Therefore, the voltage application detection unit 122 switched in the high impedance state can accurately detect the amount of change and accurately detect the impedance. As a result, the control device 100 is configured to detect the impedance of each of the high impedance state and the low impedance state by an appropriate one of the voltage application detection unit 122 and the current application detection unit 123. Therefore, the control device 100 is configured to inhibit a decrease in the detection accuracy of the impedance of the air-fuel ratio sensor 10.

According to the improvement of the impedance detection accuracy in the low-temperature state, the decrease in the impedance detection accuracy can be inhibited even in the low-temperature state at the start of the engine driving. Further, even when the temperature becomes low due to the stop of the exhaust gas from the engine at the time of driving the motor, the deterioration of the detection accuracy of the impedance at the time of resuming the driving of the engine can be inhibited. Therefore, the operation of the heater for the purpose of maintaining a target temperature at the time of driving the motor can be inhibited.

Second Embodiment

Figure 8:
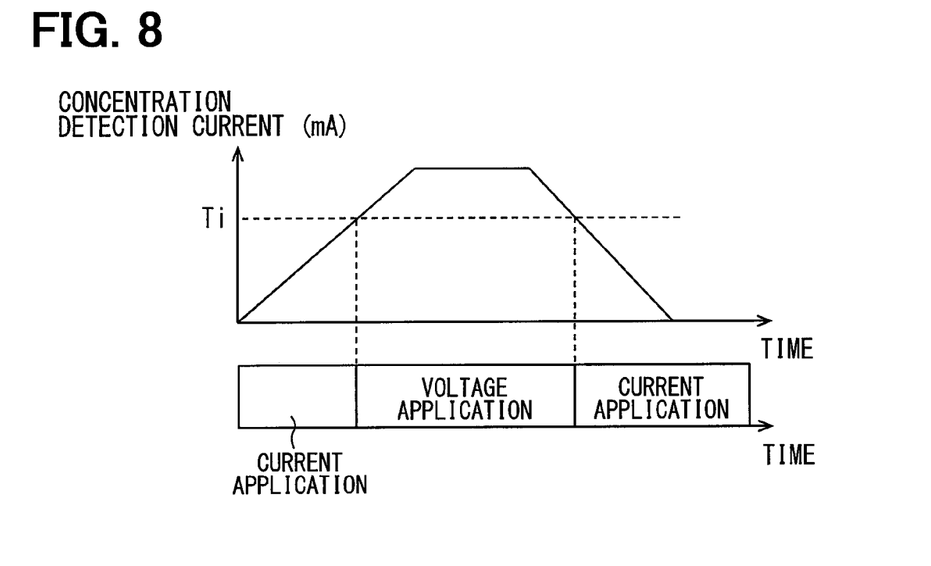
FIG. 8 is a diagram showing an example of a switching behavior according to a second embodiment.
Figure 9:
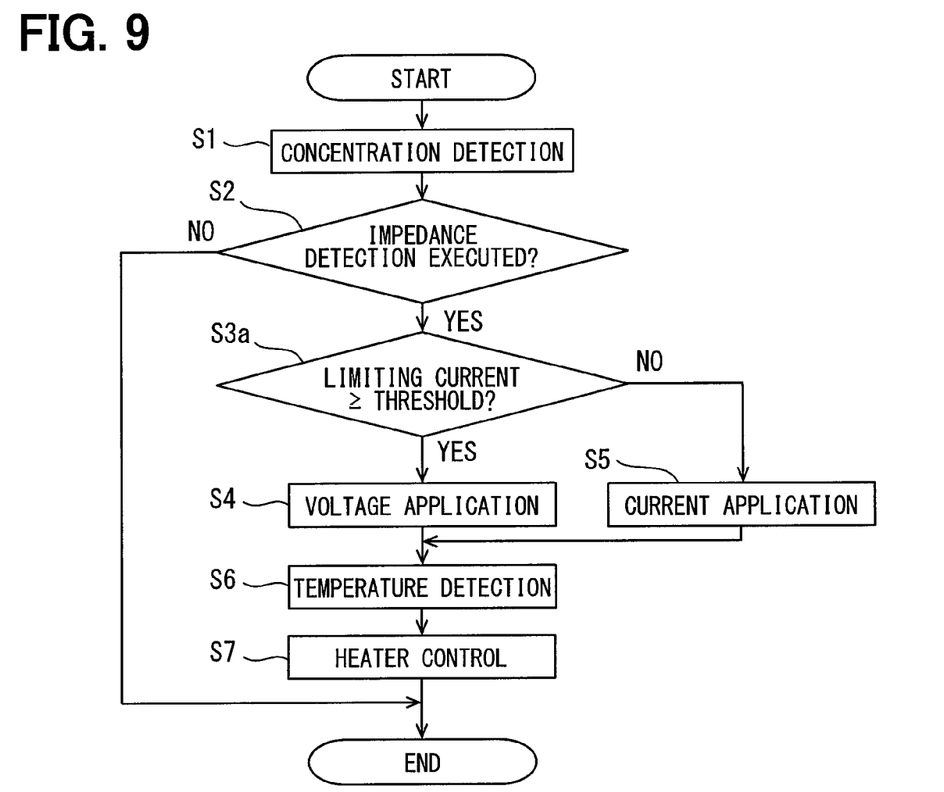
FIG. 9 is a flowchart showing the processing of a calculation unit according to the second embodiment.

A second embodiment shown in FIGS. 8 and 9 is a modification of the first embodiment. In a control device 100 according to the second embodiment, the operation of a detection switching unit 124 (refer to FIG. 1) is different from the operation in the first embodiment.

The detection switching unit 124 according to the second embodiment switches between a voltage application detection unit 122 and a current application detection unit 123 based on a concentration detection current detected by the concentration detection unit 121. As shown in FIG. 8, the detection switching unit 124 performs switching based on whether the detected concentration detection current is a large current state in which the detected concentration detection current is equal to or larger than a current threshold Ti or a small current state in which the detected concentration detection current is smaller than the current threshold Ti.

The current threshold Ti is set to, for example, a maximum value of the concentration detection current detected by the application of a predetermined voltage at a minimum temperature at which an air-fuel ratio sensor 10 can be regarded as an active state. The detection switching unit 124 causes the current application detection unit 123 to detect an impedance when a duration of the small current state is equal to or longer than a predetermined time. The detection switching unit 124 causes the voltage application detection unit 122 to detect the impedance when the current state is a large current state or when the duration of the small current state is shorter than the predetermined time.

An example of a processing procedure in the calculation unit 120 according to the second embodiment will be described. Instead of the processing shown in FIG. 7, the calculation unit 120 periodically executes the processing shown in FIG. 9 in order from S1. The processing of S1, S2, and S4 to S7 is the same as the processing shown in FIG. 7.

In S3a, it is determined whether or not the concentration detection current in the most recent predetermined number of times among the concentration detection currents detected in S1 is equal to or larger than a current threshold by the processing corresponding to the detection switching unit 124. For example, if the concentration detection current is equal to or larger than the current threshold by one or more times, the routine proceeds to S4, and if the concentration detection current is less than the current threshold all in all, the routine proceeds to S5.

According to the second embodiment described above, similarly to the first embodiment, the impedance can be detected by an appropriate detection unit corresponding to the state of the air-fuel ratio sensor 10. Therefore, the control device 100 is configured to inhibit a decrease in the detection accuracy of the impedance of the air-fuel ratio sensor 10.

In the second embodiment, the detection switching unit 124 switches between the voltage application detection unit 122 and the current application detection unit 123 based on the concentration detection current. The concentration detection current may change in conjunction with a change in impedance caused by a change in temperature of the air-fuel ratio sensor 10. Therefore, the control device 100 is configured to detect the impedance of the air-fuel ratio sensor 10 by an appropriate one of the voltage application detection unit 122 and the current application detection unit 123 in accordance with the impedance of the air-fuel ratio sensor 10. Therefore, the control device 100 is configured to inhibit a decrease in the detection accuracy of the impedance of the air-fuel ratio sensor 10.

In addition, according to the second embodiment, the detection switching unit 124 switches between the current application detection unit 123 and the voltage application detection unit 122 based on whether the current is in the large current state or the small current state. In this example, whether or not a large current flows can be interlocked with the switching of the high impedance state and the low impedance state caused by the temperature change of the air-fuel ratio sensor 10. As a result, the control device 100 is configured to detect the impedance of each of the high impedance state and the low impedance state by an appropriate one of the voltage application detection unit 122 and the current application detection unit 123. Therefore, the control device 100 is configured to inhibit a decrease in the detection accuracy of the impedance of the air-fuel ratio sensor 10.

Further, according to the second embodiment, the detection switching unit 124 switches to the current application detection unit 123 based on the small current state, and switches to the voltage application detection unit 122 based on the large current state. In this example, the small current state may occur with a high impedance state caused by the low temperature of the air-fuel ratio sensor 10. In addition, the large current state may occur with a low impedance state caused by the high temperature of the air-fuel ratio sensor 10. As a result, the control device 100 is configured to detect the impedance by an appropriate one of the voltage application detection unit 122 and the current application detection unit 123 in accordance with the impedance of the air-fuel ratio sensor 10. Therefore, the control device 100 is configured to inhibit a decrease in the detection accuracy of the impedance of the air-fuel ratio sensor 10.

Third Embodiment

Figure 10:
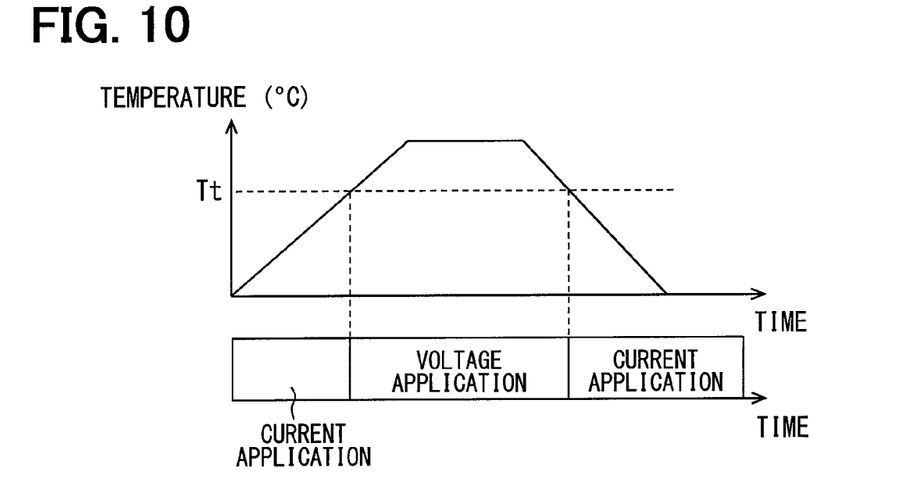
FIG. 10 is a diagram showing an example of a switching behavior according to a third embodiment.
Figure 11:
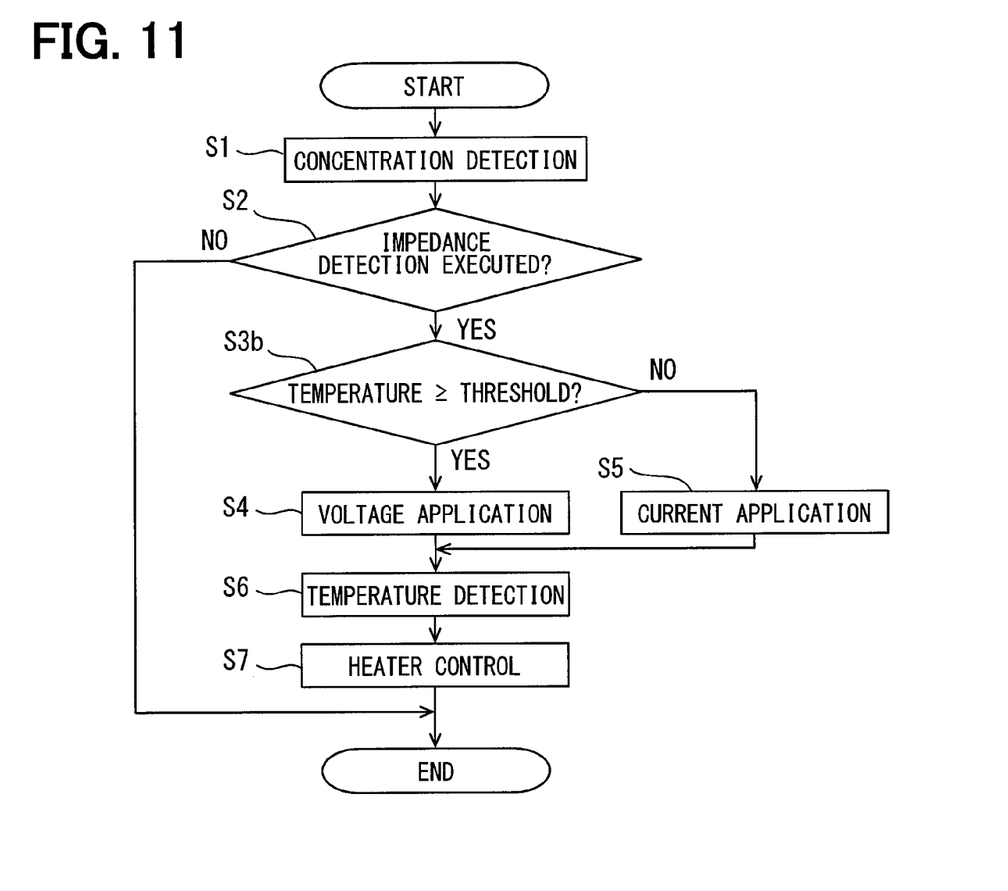
FIG. 11 is a flowchart showing the processing of a calculation unit according to the third embodiment.

A third embodiment shown in FIGS. 10 and 11 is another modification of the first embodiment. In a control device 100 according to the third embodiment, the operation of a detection switching unit 124 (refer to FIG. 1) is different from the operation in the first embodiment.

The detection switching unit 124 according to the third embodiment switches to a detection unit that next detects an impedance based on a temperature of an air-fuel ratio sensor 10 estimated by a temperature detection unit 125. As shown in FIG. 10, the detection switching unit 124 performs switching based on whether the detected temperature is a high-temperature state equal to or higher than a temperature threshold Tt or a low-temperature state less than the temperature threshold Tt.

The temperature threshold Tt is set to, for example, a minimum temperature at which the air-fuel ratio sensor 10 can be regarded as an active state. The detection switching unit 124 causes the current application detection unit 123 to detect an impedance in the low-temperature state. The detection switching unit 124 causes the voltage application detection unit 122 to detect the impedance in the high-temperature state.

An example of a processing procedure in the calculation unit 120 according to the third embodiment will be described. Instead of the processing shown in FIG. 7, the calculation unit 120 periodically executes the processing shown in FIG. 11 in order from S1. The processing of S1, S2, and S4 to S7 is the same as the processing shown in FIG. 7.

In S3b, it is determined whether or not the temperature detected in the most recent S6 is equal to or higher than the temperature threshold by the processing corresponding to the detection switching unit 124. If the detected temperature is equal to or higher than the temperature threshold, the routine proceeds to S4, and if the temperature is not equal to or higher than the temperature threshold, the routine proceeds to S5. If the state is immediately after the start of the periodic execution of FIG. 11, it is determined that the temperature is not equal to or greater than the temperature threshold, and the routine proceeds to S5.

According to the third embodiment described above, similarly to the first embodiment, the impedance can be detected by an appropriate detection unit according to the state of the air-fuel ratio sensor 10. Therefore, the control device 100 is configured to inhibit a decrease in the detection accuracy of the impedance of the air-fuel ratio sensor 10.

According to the third embodiment, the detection switching unit 124 switches between the voltage application detection unit 122 and the current application detection unit 123 based on the temperature of the air-fuel ratio sensor 10. The change in temperature may change the impedance of the air-fuel ratio sensor 10. Therefore, the control device 100 is configured to detect the impedance of the air-fuel ratio sensor 10 by an appropriate one of the voltage application detection unit 122 and the current application detection unit 123 in accordance with the impedance of the air-fuel ratio sensor 10. Therefore, the control device 100 is configured to inhibit a decrease in the detection accuracy of the impedance of the air-fuel ratio sensor 10.

Further, according to the third embodiment, the detection switching unit 124 switches between the current application detection unit 123 and the voltage application detection unit 122 based on whether the detected temperature is in the high-temperature state or the low-temperature state. In this example, the switching between the high-temperature state and the low-temperature state may be interlocked with the switching between the high impedance state and the low impedance state. As a result, the control device 100 is configured to detect the impedance of each of the high impedance state and the low impedance state by an appropriate one of the voltage application detection unit 122 and the current application detection unit 123. Therefore, the control device 100 is configured to inhibit a decrease in the detection accuracy of the impedance of the air-fuel ratio sensor 10.

In addition, according to the third embodiment, the detection switching unit 124 switches to the voltage application detection unit 122 in the high-temperature state, and switches to the current application detection unit 123 in the low-temperature state. In this example, in the low-temperature state, the air-fuel ratio sensor 10 is in the high impedance state. In the high-temperature state, the air-fuel ratio sensor 10 is in the low impedance state. As a result, the control device 100 is configured to detect the impedance by an appropriate one of the voltage application detection unit 122 and the current application detection unit 123 in accordance with the impedance of the air-fuel ratio sensor 10. Therefore, the control device 100 is configured to inhibit a decrease in the detection accuracy of the impedance of the air-fuel ratio sensor 10.

Other Embodiments

Although the embodiments of the present disclosure have been described above, the present disclosure is not limited to the embodiments described above, and the following modifications are included in the technical scope of the present disclosure, and can be implemented by various modifications within a scope not departing from the spirit of the present disclosure in addition to modifications described below. In the following description, elements having the same reference numerals as those used so far are the same as elements having the same reference numerals in the previous embodiments, except when specifically mentioned. When only a part of the configuration is described, the embodiment described above can be applied to other parts of the configuration.

In the embodiments described above, the calculated impedance is used for calculating the temperature used for controlling the heater or the like. However, the calculated impedance may be used for estimation of degradation of the air-fuel ratio sensor 10.

In the embodiments described above, the concentration detection unit 121 sets the predetermined voltage to be applied to the air-fuel ratio sensor 10 for oxygen concentration detection to be substantially constant. However, the concentration detection unit 121 may be configured to adjust the applied voltage based on the temperature of the air-fuel ratio sensor 10, the flowing current, and the like.

In the embodiments described above, the impedance threshold, the current threshold, and the temperature threshold are fixed values set in advance on the basis of the temperature in the active state. Alternatively, the impedance threshold, the current threshold, and the temperature threshold may be set based on other criteria. Further, those thresholds may be automatically adjusted based on the deterioration state of the air-fuel ratio sensor 10 or the like.

In the embodiments described above, the current application detection unit 123 sets the pulsed current to be applied to the air-fuel ratio sensor 10 to a fixed magnitude. However, the pulsed current is not limited to the fixed magnitude. In other words, the current application detection unit 123 may change the magnitude of the current for each pulse. The magnitude of each pulse is adjusted based on, for example, the magnitude of the impedance detected immediately before. Specifically, as the impedance increases more, the pulse is adjusted to be smaller. According to such a configuration, the voltage change amount ΔVout associated with the supply of the current can increase at a small increase rate relative to the increase rate of the impedance as the impedance increases. Therefore, the voltage change amount ΔVout is unlikely to fall outside the range detectable by the voltage detection unit 116.

In the third embodiment described above, the detection switching unit 124 switches between the detection units based on the sensor temperature detected based on the impedance in the temperature detection unit 125. However, the detection switching unit 124 may switch between the detection units based on the sensor temperature estimated with the use of the operating state of the internal combustion engine, the exhaust gas temperature, or the like.

In the embodiments described above, the shunt resistor 114 and the voltage variation unit 112 are connected to the exhaust side electrode 11, and the voltage application unit 111 and the current application unit 113 are connected to the exhaust side electrode 11. However, the exhaust side electrode 11 and the respective components connected to the exhaust side electrode 11 can replace the terminal to be connected to another terminal as appropriate. In the embodiments described above, an example of the oxygen sensor having two terminals has been described, but an oxygen sensor having three terminals may be used.

In the embodiment described above, the voltage detection unit 116 is provided separately from the current detection unit 115. However, the input to the AD converter or the like used in the current detection unit 115 may be temporally switched and temporarily used as the voltage detection unit 116.

In the embodiments described above, the detection switching unit 124 switches to the current application detection unit 123 in the high impedance state, the small current state, or the low-temperature state. However, the switching condition is not limited to the above example.

In the embodiments described above, the control device 100 is used in the hybrid vehicle having an engine and a motor as a travel driving source. However, the situation in which the control device 100 is configured to be used is not limited to the above example. For example, the control device 100 is configured to also be used in a vehicle having only an engine as the travel driving source.

In the embodiments described above, an example has been described in which the oxygen sensor is the air-fuel ratio sensor 10 used for detecting the air-fuel ratio. However, the oxygen sensor may be an O2 sensor used to determine whether the air-fuel ratio is rich or lean. The O2 sensor is formed by stacking, for example, a solid electrolyte layer, an electrode sandwiching the solid electrolyte layer, and a heater. The O2 sensor provides the exhaust gas to one electrode and the atmosphere to the other electrode, to thereby output a signal corresponding to the oxygen concentration of the exhaust gas. More specifically, the O2 sensor outputs a voltage equal to or higher than the threshold for the oxygen concentration when the air-fuel ratio is rich, and outputs a voltage lower than the threshold for the oxygen concentration when the air-fuel ratio is lean. In such an O2 sensor, similarly to the air-fuel ratio sensor 10, the impedance increases exponentially as the temperature of the solid electrolyte layer decreases.

It should be appreciated that while the processes of the embodiments of the present disclosure have been described herein as including a specific sequence of steps, further alternative embodiments including various other sequences of these steps and/or additional steps not disclosed herein are intended to be within the steps of the present disclosure.

The controllers and methods described in the present disclosure may be implemented by a special purpose computer created by configuring a processor programmed to execute one or more particular functions embodied in computer programs. Alternatively, the apparatuses and methods described in the present disclosure may be implemented by special purpose hardware logic circuits. Further alternatively, the apparatuses and methods described in the present disclosure may be implemented by a combination of one or more special purpose computers created by configuring a processor executing computer programs and one or more hardware logic circuits. The computer programs may be stored, as instructions being executed by a computer, in a tangible non-transitory computer-readable medium.

While the present disclosure has been described with reference to preferred embodiments thereof, it is to be understood that the disclosure is not limited to the preferred embodiments and constructions. The present disclosure is intended to cover various modification and equivalent arrangements. In addition, while the various combinations and configurations, which are preferred, other combinations and configurations, including more, less or only a single element, are also within the spirit and scope of the present disclosure.

What is claimed is:

1. An oxygen sensor control device configured to control an oxygen sensor, the oxygen sensor configured to output a signal corresponding to a concentration of oxygen, the oxygen sensor control device comprising:
   a voltage application detection unit configured to detect an impedance of the oxygen sensor based on a current change amount in the oxygen sensor caused by application of a voltage to the oxygen sensor;
   a current application detection unit configured to detect the impedance based on a voltage change amount generated across the oxygen sensor caused by application of a current to the oxygen sensor; and
   a detection switching unit configured to switch between the voltage application detection unit and the current application detection unit to detect the impedance based on a state of the oxygen sensor, wherein
   the detection switching unit is configured to switch between the voltage application detection unit and the current application detection unit based on the impedance.

2. The oxygen sensor control device according to claim 1, wherein
   the detection switching unit is configured to switch between the voltage application detection unit and the current application detection unit based on whether or not the impedance is equal to or higher than an impedance threshold.

3. The oxygen sensor control device according to claim 2, wherein
   the detection switching unit is configured
   to switch to the current application detection unit when the impedance is a high impedance state in which the impedance is equal to or higher than the impedance threshold and
   to switch to the voltage application detection unit when the impedance is lower than the impedance threshold.

4. An oxygen sensor control device configured to control an oxygen sensor, the oxygen sensor configured to output a signal corresponding to a concentration of oxygen, the oxygen sensor control device comprising:
   a voltage application detection unit configured to detect an impedance of the oxygen sensor based on a current change amount in the oxygen sensor caused by application of a voltage to the oxygen sensor;
   a current application detection unit configured to detect the impedance based on a voltage change amount generated across the oxygen sensor caused by application of a current to the oxygen sensor;
   a detection switching unit configured to switch between the voltage application detection unit and the current application detection unit to detect the impedance based on a state of the oxygen sensor; and
   a concentration detection unit configured to detect the concentration of oxygen based on a concentration detection current flowing through the oxygen sensor, wherein
   the detection switching unit is configured to switch between the voltage application detection unit and the current application detection unit based on the concentration detection current.

5. The oxygen sensor control device according to claim 4, wherein
   the detection switching unit is configured to switch between the voltage application detection unit and the current application detection unit based on whether or not the concentration detection current is equal to or greater than a current threshold.

6. The oxygen sensor control device according to claim 5, wherein
   the detection switching unit is configured
   to switch to the voltage application detection unit based on condition that the concentration detection current is in a large current state in which the concentration detection current is equal to or higher than the current threshold and
   to switch to the current application detection unit based on condition that the concentration detection current is in a small current state in which the concentration detection current is lower than the current threshold.

7. An oxygen sensor control device configured to control an oxygen sensor, the oxygen sensor configured to output a signal corresponding to a concentration of oxygen, the oxygen sensor control device comprising:
   a voltage application detection unit configured to detect an impedance of the oxygen sensor based on a current change amount in the oxygen sensor caused by application of a voltage to the oxygen sensor;
   a current application detection unit configured to detect the impedance based on a voltage change amount generated across the oxygen sensor caused by application of a current to the oxygen sensor;
   a detection switching unit configured to switch between the voltage application detection unit and the current application detection unit to detect the impedance based on a state of the oxygen sensor; and
   a temperature detection unit configured to detect a temperature of the oxygen sensor, wherein
   the detection switching unit is configured to switch between the voltage application detection unit and the current application detection unit based on the temperature.

8. The oxygen sensor control device according to claim 7, wherein
   the detection switching unit is configured to switch between the voltage application detection unit and the current application detection unit based on whether the oxygen sensor is in a high-temperature state in which the temperature is equal to or higher than a temperature threshold or a low-temperature state in which the temperature is lower than the temperature threshold.

9. The oxygen sensor control device according to claim 8, wherein
   the detection switching unit is configured
   to switch to the voltage application detection unit when the oxygen sensor is in the high-temperature state and to switch to the current application detection unit when the oxygen sensor is in the low-temperature state.

* * * * *